United States Patent [19]

Beekil

[11] Patent Number: 4,962,762
[45] Date of Patent: Oct. 16, 1990

[54] MODULAR SELF-CONTAINED ORTHOTIC DEVICE

[76] Inventor: Steven L. Beekil, 3333 W. Peterson, Chicago, Ill. 60659

[21] Appl. No.: 313,230

[22] Filed: Feb. 21, 1989

[51] Int. Cl.$^5$ .............................................. A61F 5/14
[52] U.S. Cl. ...................................... 128/595; 36/44
[58] Field of Search ............... 128/595, 586; 36/44, 36/71, 88

[56] References Cited

U.S. PATENT DOCUMENTS

| | | | |
|---|---|---|---|
| 2,092,909 | 9/1937 | Daniels | 128/595 |
| 3,121,430 | 2/1964 | O'Reilly | 128/595 |
| 3,325,920 | 6/1967 | Werner et al. | 128/595 |
| 3,333,353 | 8/1967 | Garcia | 128/595 |
| 3,782,390 | 1/1974 | Johnson | 128/595 |
| 3,905,376 | 9/1975 | Johnson et al. | 128/595 |
| 3,914,881 | 10/1975 | Striegel | 36/44 |
| 4,128,951 | 12/1978 | Tansill | 36/44 |
| 4,211,019 | 7/1980 | McCafferty | 128/595 |
| 4,272,898 | 6/1981 | Tansill | 36/44 |
| 4,520,581 | 6/1981 | Irwin et al. | 36/88 |
| 4,574,793 | 3/1986 | Lee et al. | 128/90 |
| 4,817,590 | 4/1989 | Stancik, Jr. | 128/90 |

FOREIGN PATENT DOCUMENTS 00268741 9/1979 European Pat. Off. .
335629 10/1930 United Kingdom ................ 128/595

Primary Examiner—Edgar S. Burr
Assistant Examiner—Tonya Lamb
Attorney, Agent, or Firm—Dick and Harris

[57] ABSTRACT

A modular self-contained orthotic device which is relatively simple and safe to construct, so as to enable one in need of such a device to cause the orthotic to be made quickly and inexpensively. The device comprises a housing member which encases a resilient impression material impregnated with a chemical curing agent. The housing and impression material are internally positioned in the bottom of an enclosure element which secures the entire device on to, and around, a user's foot. The impression material conforms to, and hardens in the shape of, the user's foot as the result of the introduction of a liquid medium which reacts with the curing agent impregnated into the resilient material. After the previously resilient material has hardened, the user may withdraw his/her foot from the orthotic. The resulting hardened casting may then be trimmed, cleaned and resurfaced for actual use as an orthotic in an individual's shoe.

10 Claims, 1 Drawing Sheet

U.S. Patent
Oct. 16, 1990
4,962,762
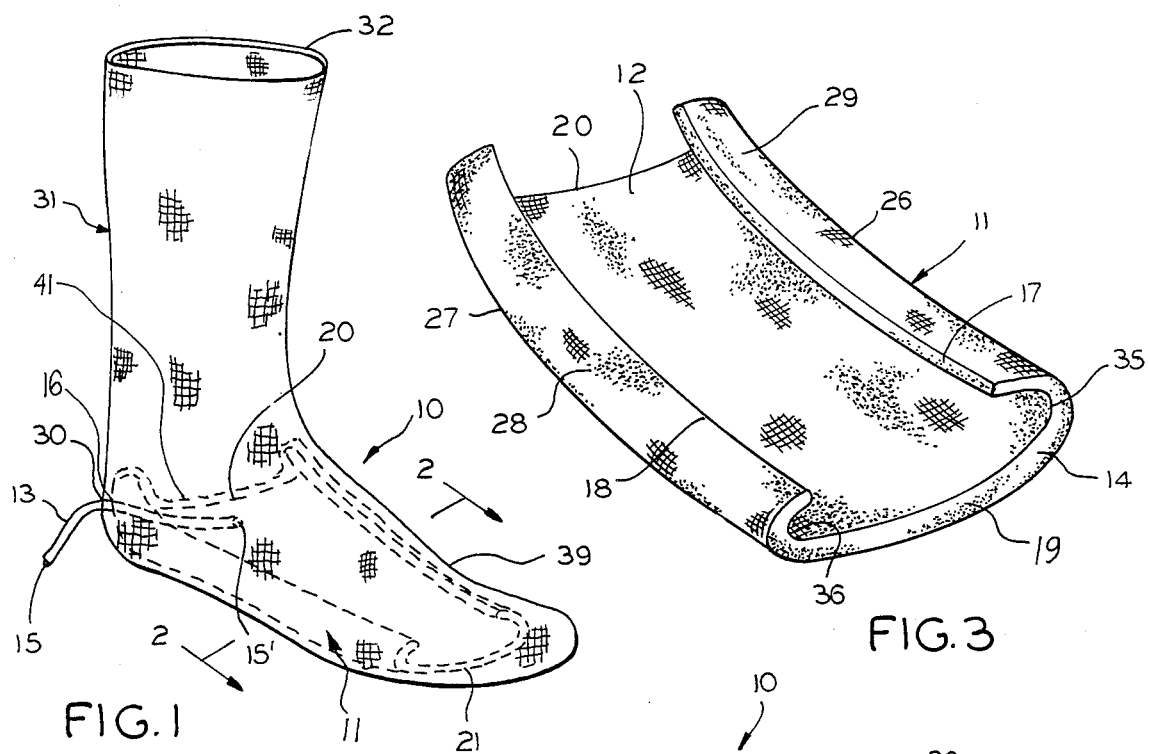
FIG.1
FIG.3
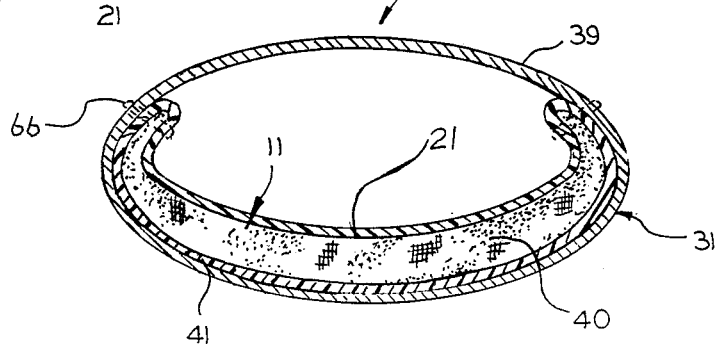
FIG.2
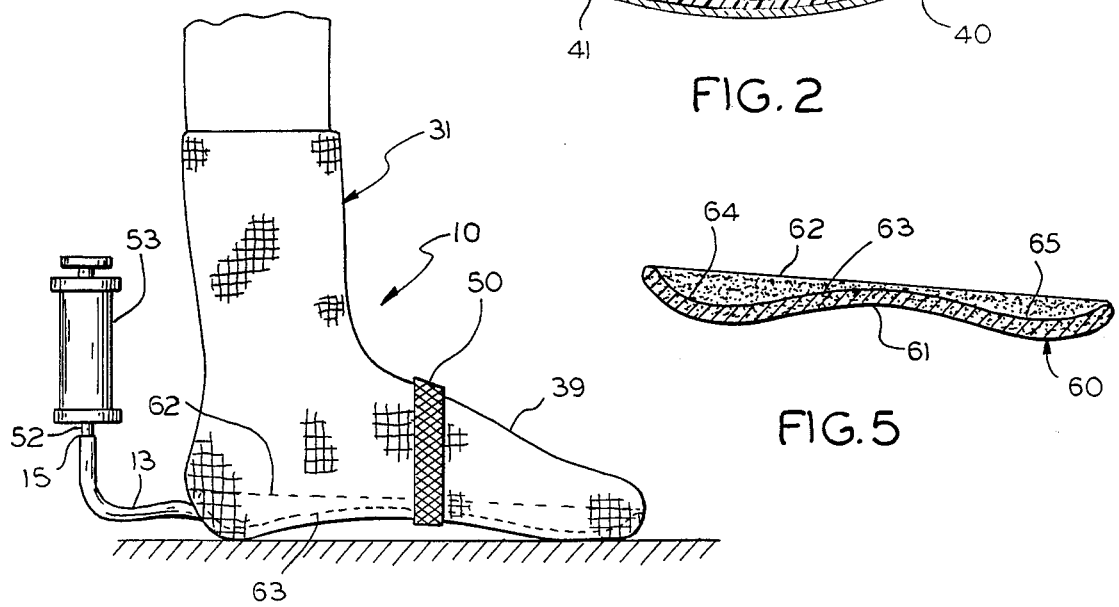
FIG.4
FIG.5

MODULAR SELF-CONTAINED ORTHOTIC DEVICE

BACKGROUND OF THE INVENTION

The present invention relates in general to orthotic devices, and, in particular, to a modular self-contained orthotic device which can be made under a doctor's supervision or, in the alternative at a patient's home with little supervision. The present invention is constructed with a foot enclosure element, which may be constructed and configured substantially similar to a conventional sock, and a plastic housing (located at the bottom of the foot enclosure element) which encases some fiberglass-gauze. The gauze is impregnated with a hardening agent, which, when injected with a liquid reactant, starts a curing process which ultimately hardens the gauze. The injection of the reactant is not introduced until just prior to the time when the person in need of the orthotic is about to insert his/her foot into the device.

After the foot is inserted, the weight applied upon the foot and, in turn, the gauze, forces the resilient gauze to conform to the contour of the bottom of the person's foot. After only a matter of minutes, the gauze is substantially cured, and the user can remove his/her foot from the device. The device can be further trimmed or covered so that any rough edges of the orthotic are removed or smoothed.

Historically, people in need of corrective devices for feet and shoes have had to expend great amounts of time and money by going to, and waiting at, a doctor's office for purposes of having an orthotic made for their foot. Typically, such devices required a two step process where first, a model of the foot is made from a plaster cast impression, followed by molding a plastic appliance about the model of the foot. While such orthotics utilized in the past by doctors have been quite effective, few, if any, have been designed in such a way where the actual orthotic creation process can be performed efficiently and inexpensively away from the doctor's office or facility.

Few if any prior art devices enable such a process to be performed while reducing the risk of error which occassionally occurs as a result of using conventional casting boxes or two-stage casting techniques during such orthotic formation. A relevant prior art device which has relied upon the use of an impregnated foot impression member, for use as a corrective device to be inserted into a shoe or boot, is U.S. Pat. No. 4,520,581. However, this particular art, is not constructed to be utilized outside of a medical facility, or outside of a special fixture-like casting device. Furthermore, few, if any, prior art devices provide for such an orthotic to be created, as well as transported in a "sock" like enclosure which is light weight, inexpensive and designed to assist in conforming to the contour of a human foot.

It is thus an object of the present invention to provide a modular self-contained orthotic device which can be used at a doctor's facility or, in the alternative, at the home of the person in need of the orthotic, while further enabling exceptional ease in the apparatuses application—in an environment in which a two-stage casting process is eliminated.

It is additionally an object of the present invention to provide a modular self-contained orthotic device which is securely encased within a housing, and positioned within an external foot enclosure element—wherein the foot enclosure element comprises a resilient material which snugly, yet comfortably conforms to and around the user's foot, so as to ensure creation of an accurate in-shoe orthotic.

It is still further an object of the present invention to provide a modular self-contained orthotic device which is relatively simple, safe, and clean to use, so as to make home use desirable to a patient.

Still another object of the present invention is to provide a modular self-contained orthotic device which is relatively inexpensive to make.

These and other objects of the present invention shall become apparent from the following specifications, claims and drawings.

SUMMARY OF THE INVENTION

The present invention comprises a modular self-contained orthotic device for inexpensively and efficiently forming and casting an impression of the bottom portion of an individual's foot. The cast formed as a result of this impression will be utilized as an orthotic device for the individual.

The modular self-contained orthotic device includes foot enclosure means which have an internal side and an external side, which are oppositely positioned in relation to each other. The foot enclosure means additionally includes an upper portion, and a lower portion, which are integrally constructed together. The upper portion is configured so as to substantially conform to and around the bottom of the individual's leg, and the lower portion is configured so that it substantially conforms to fit around the individual's foot. A substantially liquid-tight housing means is positioned within the foot enclosure means. This housing means has longitudinal sides, an external surface and a substantially sealed internal pocket means. The substantially liquid-tight housing means is operably positioned between the individual's foot and the foot enclosure means. Substantially flexible impression means are operably positioned within the internal pocket means of the liquid-tight housing means. The flexible impression means is disposed to describe a substantially flat foot impression surface, and a substantially flat base surface which is positioned opposite to the foot impression surface. This foot impression surface may be operably positioned adjacent to the bottom of the individual's foot. The base surface, is juxtaposed to the lower most internal side of the foot enclosure means. In addition, the substantially flexible impression means is impregnated with a hardening agent which reacts upon introduction of a liquid medium.

Once a chemical reaction between the hardening agent and liquid medium starts to occur, the substantially flexible impression means is converted, in a matter of minutes, into a rigid impression member. Conduit means are operably attached to the impression means which is ultimately located within the foot enclosure means. The conduit actually serves to channel a desired quantity of the liquid medium, so as to enable the hardening process of the substantially flexible impression means to occur. The conduit means further includes propulsion means which is operably attached thereto for propelling the liquid medium through the conduit means and into the liquid-tight housing means. Once this liquid medium is properly propelled into the liquid-tight housing means, the substantially flexible impression means begins to harden into a cast of the individual's foot bottom. The formation occurs by the individual applying pressure upon the substantially flexible impression means while the liquid medium reacts with the hardening agent means to solidify same, into a solid cured orthotic member.

In a preferred embodiment of the invention, the modular self-contained orthotic device further includes arch securement means which are operably applied around the external side of the lower portion of the foot enclosure means. This arch securement means serves to restrain the modular self-contained orthotic device from any inadvertent movement which may occur while the impression is being made. At the same time, such securement serves to improve the impression of the foot bottom into the flexible impression means.

In this preferred embodiment of the invention, the arch securement means comprises a substantially elastomeric band which enables the arch securement means to be stretched. Accordingly, such resiliency allows the arch securement means to conform to and around any size foot inserted within the lower portion of the foot enclosure means.

In the preferred embodiment of the invention, the foot enclosure means is constructed of a substantially resilient material which enables effective securement and support of the liquid-tight housing means. This resilient material further enables the appropriate positioning of the substantially flexible impression means, when a user has applied the modular self-contained orthotic device on and about the foot and leg portions. Furthermore, the foot enclosure means can also comprise a cushioned sock.

In yet another embodiment of the invention, the liquid-tight housing means consists of a substantially flexible, transparent liquid impervious plastic material.

In still another embodiment of the invention, the conduit means comprises a substantially flexible tube shaped member which has an internal channel located therewithin. This internal channel serves to conduct the liquid medium from the propulsion means to the internal pocket means of the liquid-tight housing means. Accordingly, a uniform distribution of the liquid medium is spread throughout the flexible impression means.

In yet another embodiment of the invention, the propulsion means consists of a syringe capable of injecting the liquid medium through the conduit means, and into the internal pocket means of the liquid-tight housing means.

In the preferred embodiment of the invention, the substantially flexible impression means consists of a fiberglass-gauze material.

In still another embodiment of the invention, the impregnating hardening agent comprises polyurethane. The liquid medium which eventually comes into contact with the polyurethane comprises water.

In an alternative embodiment of the invention, the impregnating hardening agent means comprises a fast-set vinyl epoxy material, such as Ashland Chemicals' Hetron 922-20. In addition, the liquid medium used to react with the fast-set vinyl epoxy material consists of methyl ethyl ketone.

In the preferred embodiment of the invention, the flexible impression means further includes foot contour means which are operably positioned juxtaposed to the longitudinal sides of the liquid-tight housing means. These foot contour means enable the flexible impression means, and, in turn, the liquid-tight housing means to partially wrap over a portion of a user's foot, so as to restrain the flexible impression means from inappropriate alignment during the casting of same.

The present invention is constructed with a foot enclosure element, which may be constructed and configured substantially similar to a conventional sock, and a plastic housing (located at the bottom of the foot enclosure element) which encases some fiberglass-gauze. The gauze is impregnated with a hardening agent, which, when injected with a liquid reactant, starts a curing process which ultimately hardens the gauze. The injection of the reactant is not introduced until just prior to the time when the person in need of the orthotic is about to insert his/her foot into the device.

After the foot is inserted, the weight applied upon the foot and, in turn, the resilient gauze forces the gauze to conform to the contour of the bottom of the person's foot. After only a matter of minutes, the gauze is substantially cured, and the user can remove his/her foot from the device. The device can be further trimmed or covered so that any rough edges of the orthotic are removed or smoothed.

BRIEF DESCRIPTION OF THE DRAWINGS

FIG. 1 of the drawings is a front perspective view of the modular self-contained orthotic device displayed in phantom, showing, in particular, positioning of the liquid-tight housing means and flexible impression means, as well as the location of the conduit tube used for transmission of a liquid medium;

FIG. 2 of the drawings is a cross-sectional view of the invention taken along lines 2—2 of FIG. 1, and looking in the direction of the arrows, particularly showing the curved side walls of the flexible impression means and its positioning within the internal pocket of the liquid-tight housing means;

FIG. 3 of the drawings is a perspective view of the substantially flexible impression means prior to hardening, showing its curved side walls, as well as the fiberglass-gauze material impregnated with hardening agent used for same;

FIG. 4 of the drawings is an elevated side view of a user's leg and foot regions, showing in particular, placement of the invention with an arch securement band used to retain the device in a relatively stationary position upon a user's foot, as well as the propulsion and conduit means attached to the housing, for purposes of transmitting the liquid medium into the internal pocket of the housing; and FIG. 5 of the drawings is a cross-sectional view of the rigid impression member, particularly showing the contours which form as a result of the impression caused by the user's foot.

DETAILED DESCRIPTION OF THE DRAWINGS

While this invention is susceptible of embodiment in many different forms, there is shown in the drawings and will herein be described in detail, one specific embodiment with the understanding that the present disclosure is to be considered as an exemplification of the principles of the invention and is not intended to limit the invention to the embodiment illustrated.

Modular self-contained orthotic device 10 is shown in FIG. 1 as including foot enclosure means 31, housing means 41, impression means 11 and conduit 13. Foot enclosure means 31 includes aperture 32, external surface 39 and conduit entrance point 30. The conduit entrance point provides a means for insertion of conduit 13 into and through the foot enclosure means 31. An additional conduit connecting point 16, is also included on housing means 41, so as to allow second end 15' of conduit 13, to be operably located therewithin. Housing means 41 is positioned juxtaposed to the bottom area of the internal surface of enclosure means 31. Furthermore, housing means 41 is constructed with an internal pocket 21, which serves to enshroud impression means 11 therewithin.

Second end 15' of conduit 13 is positioned within internal pocket 21 of housing means 41, where it rests upon impression means 11. Such positioning is necessary so that a liquid medium can be propelled through conduit 13 and into, and on, impression means 11, prior to the hardened orthotic being created by a user thereof. The liquid medium is inserted through propulsion means 53, (as shown in FIG. 4). Propulsion means expulsion tube 52 is inserted into the first end 15 of conduit 13, so as to allow the liquid medium to pass into the conduit without the risk of leaking.

As can be seen, when impression means 11 is operably positioned within foot enclosure means 31, its heel end 20 is located juxtaposed to the heel portion of the sock-like foot enclosure means. Accordingly, front tip 14 of impression means 11, as shown in FIG. 3, is positioned juxtaposed to the foot enclosure means' toe area.

Modular self-contained orthotic device 10 is shown in a cross-sectional view in FIG. 2, as including impression means 11, foot enclosure means 31, and housing means 41. As can be seen, the impression means is operably positioned within internal pocket means 21 of housing means 41. When completely assembled, the plastic housing means 41 will abut with impression means 11, as well as foot enclosure means 31. Also shown in FIG. 2, is the hardening agent impregnated on the gauze material 40 of impression means 11. External surface 39 of foot enclosure means 31 is further revealed, as is attachment stitching 66 which may be utilized to attach enclosure 31 to housing means 41.

Impression means 11 is shown in FIG. 3 as including foot impression surface 12, base surface 27, side edges 17 and 18, heel end 20 and front tip 14. Impression means 11 itself, is made of a relatively flexible gauze material 26, which is impregnated with a hardening agent, such as powdered hardening agent 19 and 28. Because impression means 11 is relatively soft and flexible prior to the insertion of a liquid medium, its side edges, such as side edges 17 and 18, can be curled slightly over the side edges of user's foot, so as to help preclude any inadvertent slipping and/or sliding which may result during the actual formation of the orthotic 60, as shown in FIG. 5. The actual curling of impression means 11 prompts the side edges over a foot in such a way, so as to induce at least a portion of foot impression surface 12 to form contours, such as contours 35 and 36, corresponding to the lower contours or instep of a user's foot. Accordingly, a portion 29 of base surface 27 of impression means 11 is thereby actually positioned above, as opposed to below, foot impression surface 12.

FIG. 4 shows modular self-contained orthotic device 10 in its actual operating environment—wherein a human foot is inserted therewithin. In one embodiment, a liquid medium, such as methyl ethyl ketone, has been injected into internal pocket 21, as shown in FIG. 2, by forcing said liquid medium through conduit 13 by the use of propulsion means 53. Accordingly, the liquid medium saturates impression means 11, and in turn, the hardening agent, such as hardening agent 19 and 28, (such as Ashland Chemicals' Hetron 922-20) as shown in FIG. 3. It is only after the liquid medium and the hardening agent come into contact with each other that the actual curing process of the orthotic commences. In an alternative embodiment, the hardening agent comprises polyurethane for activation by a liquid medium of water.

While the curing process is going on, it becomes necessary to, restrict movement of the exerted foot for purposes of forming an effective orthotic. In addition to the use of curled edges, such as curled edges 17 and 18, as shown in FIG. 3 and mentioned hereinabove, such securement is additionally obtained by the use of a substantially elastomeric arch securement band 50, as well as the foot enclosure means 31 itself. Foot enclosure means 31 is constructed of a resilient material which enables a secure, yet comfortable fit, around the wearer's foot. Arch securement band 50 may then be operably positioned over external surface 39 of foot enclosure means 31, and accordingly, around the user's foot. As a result, when the foot is downwardly forced onto the impression means 11, impression means 11 actually conforms to the contours of the foot, as shown by contour 63. As the impression is being made, excess portions, such as excess side portion 62, is forced away from the bottom of the foot. It is this excess material which will eventually be trimmed away after impression means 11 has hardened. Also shown in FIG. 4 with propulsion means 53, is expulsion tube 52, connected to first end 15 of conduit 13. After the impression has substantially cured to the point where orthotic device 10 can be separated from the foot, foot enclosure means 31, comprising a substantially resilient, indeed elastic sock-like material, may first be removed from the user. Rigid member 60 may then be removed from housing means 41 and the housing means, together with its propulsion means 53, may be collectively discarded, or, if possible cleaned for re-use.

A cross-section of hardened, formed rigid impression member 60 is shown in FIG. 5, prior to excess material, such as excess material 62, being trimmed away. As can be seen, an effective impression of the user's foot is formed thereon. Accordingly, the rigid impression member which has resulted, actually becomes the orthotic device which includes formed contours, such as contours 64, 63, 61 and 65, which actually conform to the user's heel, arch, and ball of foot, respectively.

The foregoing description and drawings merely explain and illustrate the invention, and the invention is not limited thereto except insofar as the appended claims are so limited, as those skilled in the art who have the disclosure before them will be able to make modifications and variations therein without departing from the scope of the invention.

What is claimed is:

1. A modular self-contained orthotic device for inexpensively and efficiently forming and casting an impression of the bottom portion of an individual's foot, the casting resulting therefrom in turn being utilized as an orthotic device for said individual, said device comprising:

self-contained foot enclosure means of a substantially lightweight elastic sock-like fabric having an internal side and an external side opposite to said internal side, said foot enclosure means having an elastic upper portion and an elastic lower portion integrally attached thereto, said elastic upper portion configured so as to substantially and closely conform to and around the bottom of said individual's leg, and said lower portion configured so as to substantially and closely conform about the bottom of said individual's foot;

substantially liquid-tight housing means having longitudinal sides, an external surface and internal pocket means, said substantially liquid-tight housing means being operably positioned between said individual's foot and said internal lower portion of said foot enclosure means, with said internal pocket means being positioned below the bottom of said individual's foot;

substantially flexible impression means operably and preliminarily positioned within said internal pocket means of said liquid-tight housing means, said flexible impression means disposed to describe a substantially flat foot impression surface and a substantially flat base surface opposite said foot impression surface, wherein said foot impression surface may be operably positioned adjacent to the bottom of said individual's foot;

said substantially flexible impression means being impregnated with hardening agent means reactive to the introduction of a liquid medium to convert said substantially flexible impression means into a rigid impression member upon such introduction of said liquid medium;

conduit means operably attached to said impression means within said foot enclosure means, for channeling, as desired, quantity of said liquid medium, to in turn harden said substantially flexible impression means, said conduit means further including propulsion means operably attached thereto for propelling said liquid medium through said conduit means and into said liquid-tight housing means;

said substantially flexible impression means hardening into a casting of said individual's foot bottom, as pressure is applied thereon by said individual, while said liquid medium reacts with said hardening agent means to solidify same into a solid cured orthotic member, without reliance upon rigid casting fixtures to accomodate same.

2. The modular self-contained orthotic device according to claim 1 wherein the invention further includes arch securement means operably applied around said external side of said lower portion of said foot enclosure means so as to restrain said modular self-contained orthotic device from inadvertent movement while said impression is being made while improving the impression of the foot bottom into said flexible impression means.

3. The invention according to claim 2 wherein said arch securement means comprises a substantially elastomeric band so that said arch securement means can be stretched to conform to and around any size foot inserted within said lower portion of said foot enclosure means.

4. The invention according to claim 1 wherein said liquid-tight housing means consists of a substantially flexible, transparent liquid impervious plastic material.

5. The invention according to claim 1 wherein said medium conduit means comprises a substantially flexible tube shaped member having an internal channel therewithin so as to conduct said liquid medium from said medium propulsion means to said internal pocket means of said liquid-tight housing means, for uniform distribution throughout said flexible impression means.

6. The invention according to claim 1 wherein said medium propulsion means consists of a syringe capable of injecting said liquid medium means through said medium conduit means, and into said internal pocket means of said housing means.

7. The invention according to claim 1 wherein said substantially flexible impression means consists of a fiberglass-gauze material.

8. The invention according to claim 1 wherein said impregnating hardening agent means comprises polyurethane, said liquid medium comprising water.

9. The invention according to claim 1 wherein said impregnating hardening agent means comprises a fast-set vinyl epoxy material, said liquid medium comprising methyl ethyl ketone.

10. The invention according to claim 1 wherein said flexible impression means further includes foot contour means operably positioned juxtaposed to said longitudinal sides of said liquid-tight housing means for purposes of partially wrapping said flexible impression means, and, in turn, said liquid-tight housing means, over a portion of a user's foot, so as to restrain said flexible impression means from inappropriate alignment during the casting of same.

* * * * *